Figure 1A:
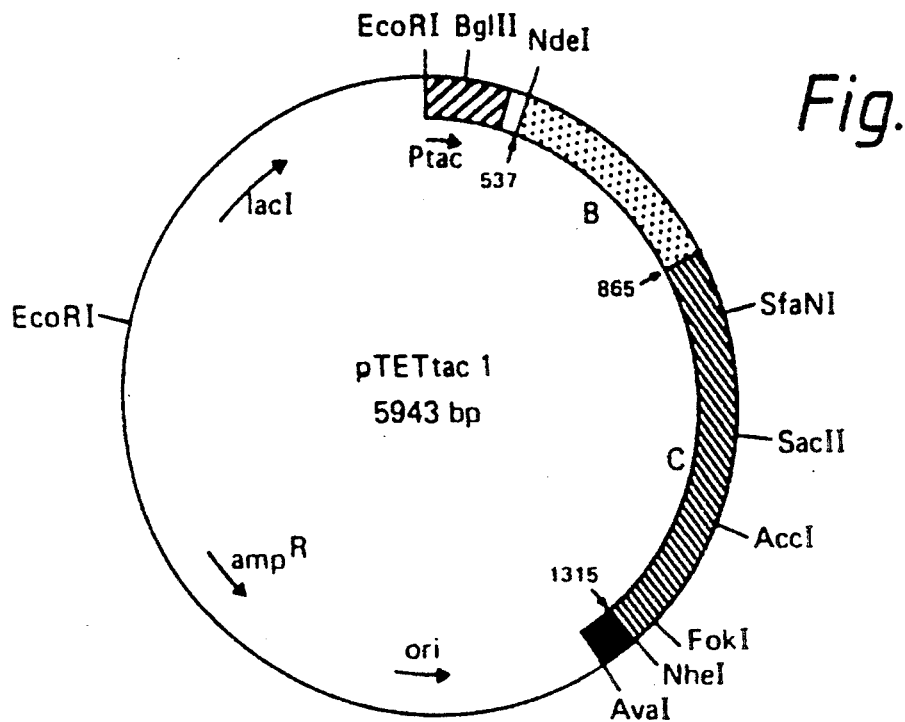

United States Patent [19]

Fairweather et al.

[11] Patent Number: 5,443,966
[45] Date of Patent: Aug. 22, 1995

[54] EXPRESSION OF TETANUS TOXIN FRAGMENT C

[76] Inventors: Neil F. Fairweather; Andrew J. Makoff, both of Langley Court, Beckenham, Kent, United Kingdom, BR 3 3BS

[21] Appl. No.: 110,786

[22] Filed: Aug. 23, 1993

Related U.S. Application Data

[63] Continuation of Ser. No. 777,337, Nov. 29, 1991, abandoned.

[30] Foreign Application Priority Data

Jun. 20, 1989 [GB] United Kingdom ............... 8914122
Jun. 20, 1990 [WO] WIPO ............... PCT/GB90/00943

[51] Int. Cl.⁶ ............... C12P 21/02; C12N 15/70; C12N 1/21
[52] U.S. Cl. ............... 435/69.3; 435/69.1; 435/252.33; 435/320.1
[58] Field of Search ............... 435/69.3, 320.1, 252.33

[56] References Cited

U.S. PATENT DOCUMENTS 4,007,265 2/1977 Helting ............... 424/92

FOREIGN PATENT DOCUMENTS 0209281 1/1987 European Pat. Off. .
2249679 5/1975 France .

OTHER PUBLICATIONS

Marston, Biochem. J. 240:1–12 (1986).
Fairweather et al, J. Bacteriol. 165:21–27 (1986).
Fairweather et al, Nuc. Acid Res. 14:7809–7812 (1986).
Fairweather et al, Infection and Immunity 55:2541–2545 (1987).
Helting et al, J. Biol. Chem. 252:187–193 (1977).
Helting et al, Act. Pathol. Microbiol. Scan. Sect. C 92:59–63 (1984).
Makoff et al, Biochem. Soc. Trans. 16:48–49 (1988).
Makoff et al, J. Gen. Microbiol. 135:11–24 (1989).
Hughes et al, J. Appl. Bact. 37:603–622 (1974).
Sheppard et al, Inf. Immun. 43:710–714 (1984).
Eisel et al, EMBO J. 5:2495–2502 (1986).
Burnette et al, Bio/Technol. 6:699–706 (1988).
Vimr et al, J. Bacteriol. 170:1495–1504 (1988).
Makoff et al, Bio/Technol. 7:1043–1046 (1989).
Halpern et al, Infection and Immunity 58:1004–1009 (1990).
Wosnick et al. (1987) Gene 60 115–127.
Shpaer (1986) J. Mol. Biol. 188:555–564.
Schein et al. (1988) Biotechnology 6:291–294.
Engels et al. (1989) Angew. Chem. Int. Ed. Engl. 28:716–734.

*Primary Examiner*—Robert A. Wax
*Assistant Examiner*—Gabriele E. Bugaisky
*Attorney, Agent, or Firm*—Nixon & Vanderhye

[57] ABSTRACT

The present invention relates to an expression vector encoding mature fragment C of tetanus toxin. The invention further relates to an *E. coli* host transformed by that vector and to a process for producing mature fragment C of tetanus toxin using same.

7 Claims, 8 Drawing Sheets

Fig. 1C

```
                     PheValProThrAspGluGlyTrpThrAsnAspSTOP
Oligo-1    5'-CTTTGTTCCAACCGATGAAGGTTGGACCAACGATTAAGGATCCG-3'
Oligo-2       3'-CAAGGTTGGCTACTTCCAACCTGGTTGCTAATTCCTAGGCGATC-5'

SD          MetLysAsnLeuAspCysTrp
Oligo-3    5'-GATCTTAATCATCCACAGGAGACTTTCTGATGAAAAACCTTGATTGTTGG
Oligo-4       3'-AATTAGTAGGTGTCCTCTGAAAGACTACTTTTTGGAACTAACAACC
```

ValAspAsnGluGluAspIleAspValIleLeuLysLysSerThrIleLeuAsnLeuAspIle
GTCGACAACGAAGAAGACATCGATGTTATCCTGAAAAAGTCTACCATTCTGAACTTGGACATC
CAGCTGTTGCTTCTTCTGTAGCTACAATAGGACTTTTTCAGATGGTAAGACTTGAACCTGTAG

AsnAsnAspIleIleSerAspIleSerGlyPheAsnSerSerValIle
AACAACGATATTATCTCCGACATCTCTGGTTTCAACTCCTCTGTTATC-3'
TTGTTGCTATAATAGAGGCTGTAGAGACCAAAGTTCAGGAGACAATAGTGTA-5'

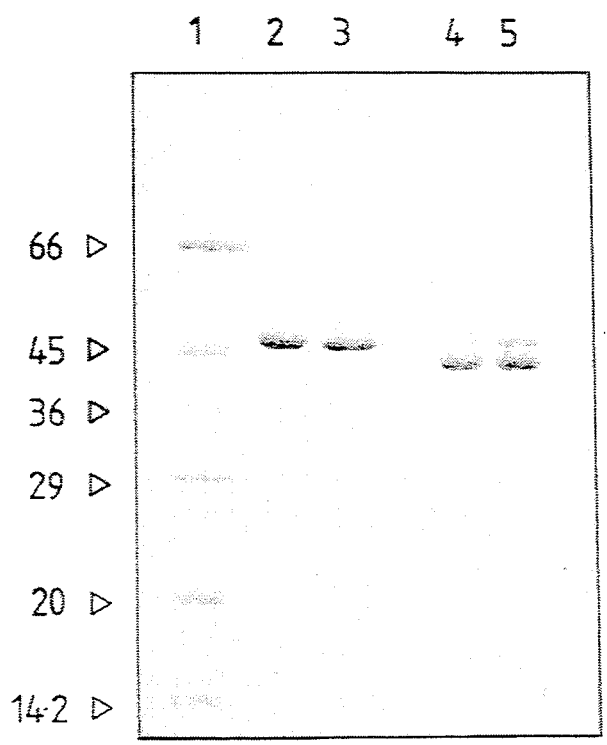
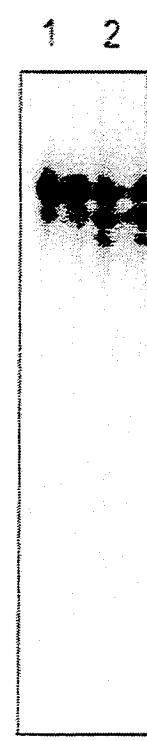
Fig. 3A
Fig. 3B

Fig. 4A

```
ATG AAA AAC CTT GAT TGT TGG GTC GAC AAC GAA GAC ATC GAT GTT ATC CTG AAA AAG   60
MET Lys Asn Leu Asp Cys Trp Val Asp Asn Glu Asp Ile Asp Val Ile Leu Lys Lys

TCT ACC ATT CTG AAC TTG GAC ATC AAC AAC GAT ATT ATC TCC GAC ATC TCT GGT TCC AAC  120
Ser Thr Ile Leu Asn Leu Asp Ile Asn Asn Asp Ile Ile Ser Asp Ile Ser Gly Phe Asn

TCC TCT AGG ATC ACA TAT CCA GAT GCT CAA TTG GTG CCC GGA ATA AAT GGC AAA GCA ATA  180
Ser Ser Val Ile Thr Tyr Pro Asp Ala Gln Leu Val Pro Gly Ile Asn Gly Lys Ala Ile

CAT TTA GTA AAC AAT GAA TCT TCT GAA GTT ATA GTG CAT AAA GCT ATG GAT ATT GAA TAT  240
His Leu Val Asn Asn Glu Ser Ser Glu Val Ile Val His Lys Ala MET Asp Ile Glu Tyr

AAT GAT ATG TTT AAT AAT TTT ACC GTT AGC TTT TGG TTG AGG GTT CCT AAA GTA TCT GCT  300
Asn Asp MET Phe Asn Asn Phe Thr Val Ser Phe Trp Leu Arg Val Pro Lys Val Ser Ala

AGT CAT TTA GAA CAA TAT GGC ACA AAT GAG TAT TCA ATA AAT AGC TCT ATG AAA AAA CAT  360
Ser His Leu Glu Gln Try Gly Thr Asn Glu Tyr Ser Ile Ile Ser Ser MET Lys Lys His
```

Fig. 4B

```
                                                                    390                                                         420
AGT CTA TCA ATA GGA TCT GGT TGG AGT GTA TCA CTT AAA GGT AAT AAC TTA ATA TGG ACT
Ser Leu Ser Ile Gly Ser Gly Trp Ser Val Ser Leu Lys Gly Asn Asn Leu Ile Trp Thr 450                                                         480
TTA AAA GAT TCC GCG GGA GAA GTT AGA CAA ATA ACT TTT AGG GAT TTA CCT GAT AAA TTT
Leu Lys Asp Ser Ala Gly Glu Val Arg Gln Ile Thr Phe Arg Asp Leu Pro Asp Lys Phe 510                                                         540
AAT GCT TAT TTA GCA AAT AAA TGG GTT TTT ATA ACT ATT ACT AAT GAT AGA TTA TCT TCT
Asn Ala Tyr Leu Ala Asn Lys Trp Val Phe Ile Thr Ile Thr Asn Asp Arg Leu Ser Ser 570                                                         600
GCT AAT TTG TAT ATA AAT GGA GTA CTT ATG GGA AGT GCA GAA ATT ACT GGT TTA GGA GCT
Ala Asn Leu Tyr Ile Asn Gly Val Leu MET Gly Ser Ala Glu Ile Thr Gly Leu Gly Ala 630                                                         660
ATT AGA GAG GAT AAT AAT ATA ACA TTA AAA CTA GAT AGA TGT AAT AAT AAT CAA TAC
Ile Arg Glu Asp Asn Asn Ile Thr Leu Lys Leu Asp Arg Cys Asn Asn Asn Gln Tyr 690                                                         720
GTT TCT ATT GAT AAA TTT AGG ATA TTT TGC AAA GCA TTA AAT CCA AAA GAG ATT GAA AAA
Val Ser Ile Asp Lys Phe Arg Ile Phe Cys Lys Ala Leu Asn Pro Lys Glu Ile Glu Lys
```

Fig.4C

```
                                                               750                                              780
TTA TAC ACA AGT TAT TCT ATA ACC TTT TTA AGA GAC TTC TGG GGA AAC CCT TTA CGA
Leu Tyr Thr Ser Tyr Leu Ser Ile Thr Phe Leu Arg Asp Phe Trp Gly Asn Pro Leu Arg 810                                              840
TAT GAT ACA GAA TAT TAT TTA ATA CCA GTA GCT TCT AGT TCT AAA GAT GTT CAA TTG AAA
Tyr Asp Thr Glu Tyr Tyr Leu Ile Pro Val Ala Ser Ser Ser Lys Asp Val Gln Leu Lys 870                                              900
AAT ATA ACA GAT TAT ATG TAT TTG ACA AAT GCG CCA TCG TAT ACT AAC GGA AAA TTG AAT
Asn Ile Thr Asp Tyr MET Tyr Leu Thr Asn Ala Pro Ser Tyr Thr Asn Gly Lys Leu Asn 930                                              960
ATA TAT AGA AGG TTA TAT AAT GGA CTA AAA TTT ATT ATA AAA AGA TAT ACA CCT AAT
Ile Tyr Arg Arg Leu Tyr Asn Gly Leu Lys Phe Ile Ile Lys Arg Tyr Thr Pro Asn 990                                              1020
AAT GAA ATA GAT TCT TTT GTT AAA TCA GGT GAT TTT ATT AAA TTA TAT GTA TCA TAT AAC
Asn Glu Ile Asp Ser Phe Val Lys Ser Gly Asp Phe Ile Lys Leu Tyr Val Ser Tyr Asn 1050                                             1080
AAT AAT GAG CAC ATT GTA GGT TAT CCG AAA GAT GGA AAT GCC TTT AAT AAT CTT GAT AGA
Asn Asn Glu His Ile Val Gly Tyr Pro Lys Asp Gly Asn Ala Phe Asn Asn Leu Asp Arg
```

Fig. 4D

```
                                                                    1110                                                               1140
ATT CTA AGA GTA GGT TAT AAT GCC CCA GGT ATC CCT CTT TAT AAA AAA ATG GAA GCA GTA
Ile Leu Arg Val Gly Tyr Asn Ala Pro Gly Ile Pro Leu Tyr Lys Lys MET Glu Ala Val 1170                                                               1200
AAA TTG CGT GAT TTA AAA ACC TAT GTA CAA CTT AAA TTA TAT GAT GAT AAA AAT GCA
Lys Leu Arg Asp Leu Lys Thr Tyr Val Gln Leu Lys Leu Tyr Asp Asp Lys Asn Ala 1230                                                               1260
TCT TTA GGA CTA GTA GGT ACC CAT AAT GGT CAA ATA GGC AAC GAT CCA AAT AGG GAT ATA
Ser Leu Gly Leu Val Gly Thr His Asn Gly Gln Ile Gly Asn Asp Pro Asn Arg Asp Ile 1290                                                               1320
TTA ATT GCA AGC AAC TGG TAC TTT AAT CAT TTA AAA GAT AAA ATT TTA GGA TGT GAT TGG
Leu Ile Ala Ser Asn Trp Tyr Phe Asn His Leu Lys Asp Lys Ile Leu Gly Cys Asp Trp

1350
TAC TTT GTT CCA ACC GAT GAA GGT TGG ACC AAC GAT TAA
Tyr Phe Val Pro Thr Asp Glu Gly Trp Thr Asn Asp ,,,
```

EXPRESSION OF TETANUS TOXIN FRAGMENT C

This is a continuation of application Ser. No. 07/777,337, filed Nov. 29, 1991, abandoned.

The present invention relates to the production of tetanus toxin C fragment.

*E. coli* has been successfully used as an host in which many foreign proteins have been obtained in large amounts. However, it has been found that the foreign protein is generally produced in an insoluble form, despite being soluble in its native environment (J.Biochem., 1986, 240, 1–12). When viewed by a microscope under phase contrast conditions, the protein aggregates are visible within the bacterial cells and are usually referred to as inclusion or refractile bodies.

It is relatively straightforward on a laboratory scale to separate inclusion bodies from the majority of *E. coli* proteins. This can be achieved for example by centrifugation and can lead to remarkable purification in just one step. However, on an industrial scale purification of the inclusion bodies is difficult to perform. In any event, to obtain the protein in an active form, the inclusion bodies have to be solubilized, requiring the use of strong denaturing agents such as urea or guanidinium chloride. The denaturant is then removed under conditions which allow the protein to refold into its native conformation. These conditions are established empirically for each protein and frequently involve the use of very dilute solutions, which on scale-up can lead to enormous volumes and consequent process engineering problems. These difficulties can be offset to some extent by the high productivity of *E. coli*, but clearly it would be desirable to obtain this benefit with the production of the protein in soluble form.

Vaccination is generally effective in the prevention of tetanus infection in most Western countries, although incomplete vaccination in some third world countries can account for up to 1 million cases of tetanus every year. Current tetanus vaccines are produced by formaldehyde treatment of tetanus toxin obtained by culture of the causative bacterium *C. tetani* under anaerobic conditions. It has been suggested that impurities arising during the formaldehyde treatment are partly responsible for the adverse effects sometimes seen with tetanus toxoid. In any event, production of the toxoid is technically difficult since it necessitates the total removal of tetanus toxin by, for example, repeated cycles of affinity purification.

The structural gene for tetanus toxin has been cloned and sequenced (Fairweather et al, J. Bacteriol. 165, 1986, 21–27; Fairweather and Lyness, Nuc. Acid Res. 14, 1986, 7809–7812). These studies have confirmed the structure of tetanus toxin as a 150 kD protein comprising 1315 amino acids. Fragment C is a 50 kD polypeptide generated by papain cleavage of the toxin and comprises, or substantially corresponds to, the 451 amino acids at the C-terminus. Fragment C has also been expressed in *E. coli* (Fairweather et al, 1986; Fairweather et al, Infection and Immunity 55, 1987, 2541–2545; EP-A-0209281) fused to part of the *E. coli* trpE protein or to fragment B of tetanus toxin. In this regard, *E. coli* strain DH1 containing pTet12, which encodes fragment C fused to part of trpE and fragment B, was deposited at the National Collection of Type Cultures, London, UK on the 28th Jun. 1985 under accession number NCTC 11918. These fusions were all insoluble in the cytoplasm of *E. coli* cells.

Fragment C has been shown to be non-toxic and is capable of immunising mice and guinea pigs (Helting and Zwisler, J. Biol. Chem. 252, 1977, 187–193; Helting and Nau, Act. Pathol. Microbiol. Scan. Sect. C 92, 1984, 59–63).

It has now been found that, when fragment C of tetanus toxin is expressed in *E. coli* in a mature form, ie. unassociated with any foreign or native polypeptide, the resulting product is substantially soluble and is not produced as inclusion bodies. Additionally, high levels of expression of the mature product can be obtained, and the product is obtained in a substantially active form, as judged by biochemical and immunological criteria.

Accordingly, the present invention provides a process for the production of fragment C of tetanus toxin, which process comprises culturing *E. coli* transformed with an expression vector encoding the mature form of fragment C and recovering the protein.

The DNA encoding mature fragment C is incorporated in the vector in the correct reading frame under the control of appropriate transcriptional and translational control elements. Examples of such elements include a promoter, a transcriptional terminator site, and of course a met start codon. An operator and/or attenuator sequence may also be present upstream of the coding sequence. Typically the expression vector is a plasmid. The promoter may be the lac, trp, $\lambda$PL, $\lambda$PR, lpp, T7$\phi$10 or tac promoter. Use of an inducible promoter, such as the tac promoter, is preferred as it enables expression to be more readily controlled. Expression of the tac promoter is induced by isopropyl-$\beta$-D-thiogalactoside (IPTG).

Example of strains of *E. coli* for use with the present invention include HB101, DH1 or MM294. The strain of *E. coli* may be transformed with the expression vector encoding mature fragment C and the transformed strain cultured using procedures known in the art.

Mature fragment C may be recovered, from the cytoplasm (in which it is dissolved) of the *E. coli* cells by lysis of the cells followed by centrifugation, acid precipitation and ion exchange chromatography. Typically the cells from a growing culture, for example from a 2.5 liter culture, are harvested by centrifugation and resuspended in a suitable buffer (e.g. 25 mM Tris/HCl pH8.0, 150 mM) NaCl containing phenylmethylsulphonyl fluoride (PMSF)). Cells are lysed by sonication, by passage through a French Pressure Cell, or by treatment with a non-ionic detergent (e.g. Nonidet NP40) and lysozyme. The lysate is centrifuged and the resulting supernatant isolated. The supernatant, containing fragment C, may then be purified using ion exchange chromatography. Fractions containing fragment C are collected and further purified until the desired degree of purity is obtained. Such further purification may involve affinity purification using monoclonal or polyclonal antibodies. Generally the degree of purity is at least 80%, preferably at least 90% and more preferably at least 95%.

As indicated earlier, fragment C is a 50 kD polypeptide derived from the C-terminus of tetanus toxin. Production in *E. coli* would of course necessitate production of the met-form of the polypeptide. Otherwise the amino acid sequence may comprise that known for fragment C or a substantially similar sequence having substantially the same biological and immunological properties. In particular, the amino acid sequence is that set forth in FIG. 4 or has at least 90%, preferably 95%, more preferably 98%, homology with that set forth in FIG. 4. Thus, within these limitations the sequence may be varied by one or more amino acid substitutions, extensions, insertions and/or deletions provided the resulting polypeptide retains substantially the same biological and immunological properties as fragment C. In the case of amino acid substitutions, one or more of the amino acid residues of fragment C may thus be replaced by one or more other amino acid residues. Candidate substitutions include Ser for Thr and vice versa, Glu for Asp and vice versa, Gln for Asn and vice versa, Leu for Ile and vice versa, Ala for Val and vice versa and Arg for Lys and vice versa.

Variations within the amino acid sequence of fragment C may of course be obtained by effecting changes in the DNA sequence encoding fragment C. This may be achieved by, for example, the use of restriction endonucleases, insertion of oligonucleotide linkers, exonucleases and/or polymerases and site-directed mutagenesis.

A vaccine for conferring immunity to tetanus comprises fragment C produced according to the invention and a pharmaceutically acceptable carrier or diluent. The vaccine may include other antigens to provide a multi-valent vaccine. Typically carriers and diluents are sterile, pyrogen-free liquid media suitable as vehicles for introducing a polypeptide into a patient. Isotonic saline solution may be employed.

The vaccine may also comprise an adjuvant for stimulating the immune response and thereby enhancing the effect of the vaccine. A convenient adjuvant is aluminium hydroxide. Conveniently the vaccines are formulated to contain a final concentration of fragment C or its derivative of from 0.2 to 200 µg/ml, preferably 5 to 50 µg/ml, most preferably about 30 µg/ml. After formulation the vaccine may be incorporated into a sterile container which is then sealed and stored at a low temperature, for example 4° C., or it may be freeze-dried.

The vaccines may be administered by any conventional method for the administration of vaccines including oral and parenteral (e.g. subcutaneous or intramuscular) injection. The treatment may consist of a single dose of vaccine or a plurality of doses over a period of time. It is recommended that each dose is 0.1 to 2 ml preferably 0.2 to 1 ml, most preferably about 0.5 ml of vaccine.

The following Example illustrates the present invention. A Comparative Example is provided. *E. coli* MM294 harbouring plasmid pTETtac1 was deposited at the National Collection of Industrial and Marine Bacteria, Aberdeen, GB on 13 Jun. 1989 under accession number NCIMB 40154.

In the accompanying drawings:

FIG. 1 shows the construction of expression plasmids pTETtac1 (a) and pTETtac2 (b) and the oligonucleotides used (c). In (a) pTETtac1 is shown as consisting of the tac promoter and modified trpD ribosome binding site ( ); the first 3 codons of the coding sequence of γ-IF ( ); the coding regions of fragments B ( ) and C ( ) of tetanus toxin; and the trpa terminator ( ). The numbers arrowed refer to amino acid positions in tetanus toxin.

Figure 2:
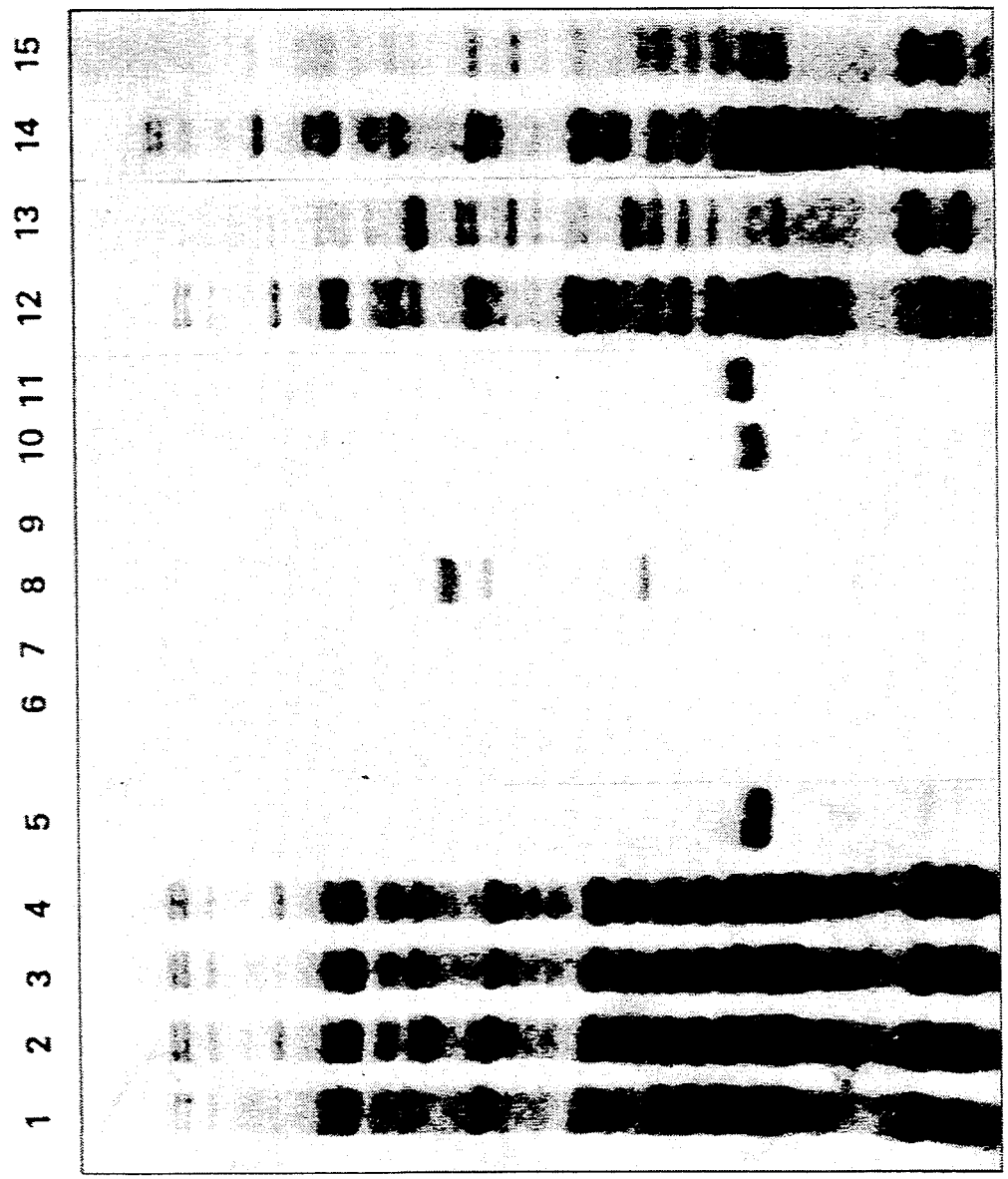

FIG. 2 shows SDS-polyacrylamide gels analysis of *E. Coli* extracts containing pTETtac1 and pTETtac2. Lanes 1–5 and 12–15 are Coomassie blue stained;. 6–11 are Western blots. Total cell extracts from pTETtac1 uninduced (lanes 1,7) and induced (lanes 2,8), pTETtac2 uninduced (lanes 3,9) and induced (lanes 4,10). Control extract (lane 6). Fragment C from *C. tetani* (lanes 5,11). pTETtac1 induced supernatant (lane 12) and pellet (lane 13). pTETtac2 induced supernatant (lane 14) and pellet (lane 15).

FIGS. 3a and 3b shows the analysis of recombinant and *C. tetani* derived fragment C by SDS-PAGE (FIG. 3A) and by non-denaturing PAGE (FIG. 3B). Samples for SDS-PAGE electrophoresis were prepared by addition to an equal volume of 2×sample buffer (14% SDS, 20% glycerol, 10% 2-mercapto-ethanol and 0.125M Tris-HCl pH 6.8). Mercaptoethanol was omitted for non-reduced samples. Samples were heated at 100° C. for 5 mins before loading. FIG. 3A: Lane 1, protein size markers (in kDa); Lane 2,3 reduced samples; Lane 4, 5 non-reduced samples; Lane 2,4 recombinant fragment C; Lane 3,5 *C. tetani* derived fragment C. Each lane contains 5 µg fragment C. Gel was stained with Coomassie brilliant blue. Samples for non-denaturing PAGE were diluted to a final concentration of 50 mM Na Cl, 10% glycerol, 5 mM Tris/HCl pH 7.5. Gels were run as described by Ballantine and Boxer, J. Bacteriol. 163, 454–459, 1985. FIG. 3B: Lane 1, recombinant fragment C; Lane 2, *C.tetani*-derived fragment C. Each lane contains 15 µg fragment C.

FIG. 4 shows the DNA and amino acid sequence of fragment C of tetanus toxin.

EXAMPLE

1. EXPERIMENTAL PROTOCOL

Construction of plasmids

Expression plasmid pTETtac1 was constructed from plasmid pPFtac1, a derivative of pIFGtac124A (Makoff and Smallwood, Biochem. Soc. Trans. 16, 1988, 48–49). The NdeI-NheI coding region of pPFtac1 was replaced by tetanus toxin coding sequence (FIG. 1a). Most of this coding sequence was provided by two restriction fragments: a NdeI-AccI 1858bp fragment from pTet1 and an AccI-FokI 442bp fragment from pTet8 (Fairweather et al, 1986). The rest of the sequence was encoded by a pair of synthetic oligonucleotides both 44 bases long, where the codon bias was optimized for expression in *E. coli*. These oligonucleotides are oligos 1 and 2 shown in FIG. 1c.

Figure 1B:
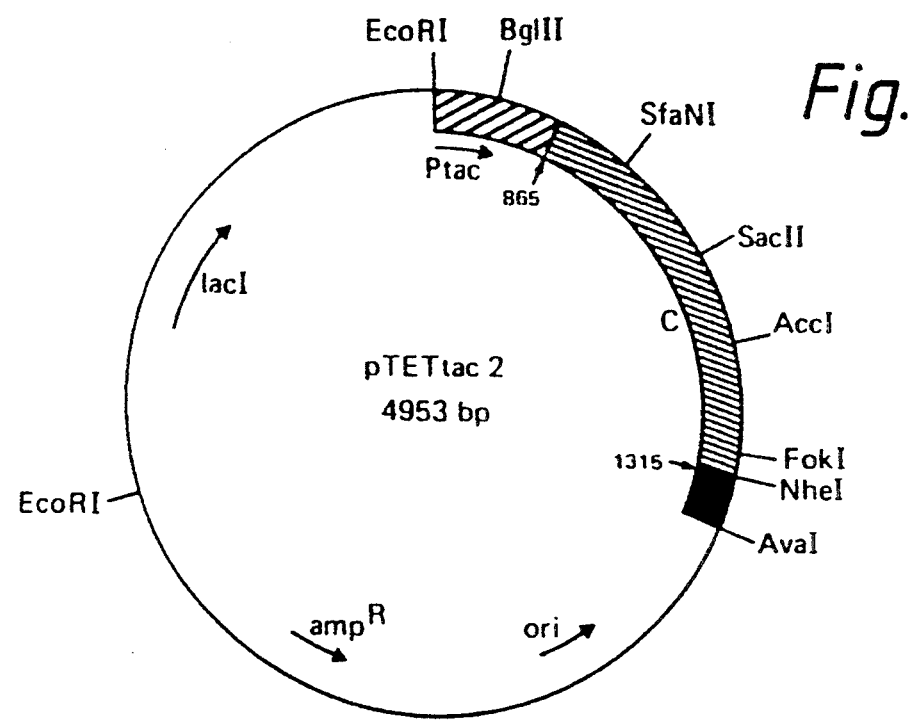

Plasmid pTETtac2 was constructed from pTETtac1 by replacing the BglII-SfaNI region of pTETtac1 by a pair of synthetic oligonucleotides each 161 nucleotides long (FIG. 1b). These oligonucleotides reproduced the sequence upstream of the initiation codon and optimised the coding sequence, at the beginning of the C fragment region, for expression in *E. coli* (FIG. 1c). The oligonucleotides were ligated to the 302 bp SfaNI-SacII and 4490 bp SacII-BglII fragments of pTETtac1.

The oligonucleotides for both constructions were synthesized in a Pharmacia Gene Assembler and purified by electrophoresis on a denaturing polyacrylamide gel. Their 5' ends were phosphorylated by T4 polynucleotide kinase before ligation. Ligated products were transformed into *E. coli* strain MM294 (Meselson and Yuan, Nature 217, 1988, 1110–1114). The sequences specified by the oligonucleotides were confirmed by direct sequencing of both plasmids pTETtac1 and pTETtac2 by the chain termination method (Sanger et al, Proc. Natl. Acad. Sci. USA 74, 1977, 5463–5467) using primers which were synthesized and purified in the same way as the oligonucleotides.

Induction and Analysis of Expressed Proteins

Cultures of *E. coli* MM294 containing the above plasmids were induced as described previously (Makoff et al, J. Gen. Microbiol. 135, 1989, 11–24) with minor alterations. Cultures were grown overnight in L broth containing 100 μg/ml ampicillin, and diluted 1 in 5 into fresh L-broth also containing 100 μg/ml ampicillin. Isopropyl-β-D-thiogalactoside (IPTG) was added to 60 μg/ml to induce expression of fragment C. The culture was harvested after 4 hours and total cell extracts were analysed on 7.5% sodium dodecyl sulphate (SDS)-polyacrylamide gels as described previously (Makoff et al, 1989). Western blots were detected by rabbit antisera against fragment C isolated from *C. tetani* and goat antirabbit IgG conjugated to horse radish peroxidase followed by Colour Development Reagent (Biorad) and hydrogen peroxide.

In order to determine if the expressed proteins were soluble, the equivalent of 1 ml cells at an OD650 of 1.0 were incubated at 0° C. for 20 mins in 100 μl 50 mM Tris-HCl pH8.0, 50 mM NaaCl, 5% glycerol, 1 mM phenylmethylsulphonylfluoride (PMSF) containing 400 μg lysozyme followed by four successive freeze-thaw cycles. Viscosity was reduced by shearing the DNA by rapid passage through a 1 ml syringe attached to a 0.8 mm bore needle. The extracts were centrifuged for 10 min at 12 k×g at 4° C. and the pellets resuspended in the same volume of the above buffer. Both pellet fractions and supernatants were centrifuged again and the resuspension repeated. Samples were diluted into 2×Laemmli loading buffer and 20 μl of each fraction was loaded onto an SDS-polyacrylamide gel and analysed as above.

Immunisation of mice

Vaccines containing fragment C from *E. coli* or *C. tetani* were prepared with 15% w/v Alhydrogel (Trade Mark). Dilutions were made as indicated in Table 1 and 0.5 ml was injected subcutaneously into NIH mice. Mice were challenged four weeks later with approximately 100 $LD_{50}$s tetanus toxin, and those mice surviving after four days were considered protected.

Purification of Recombinant Fragment C

Cell pellets (9.6 g wet wt) from 2.5 liters of culture were resuspended in about 35 mls of 25 mM Tris/HCl pH8., 150 mM NaCl containing 1 mM Phenylmethylsulphonyl fluoride (PMSF). Cell breakage was accomplished by a double passage through a pre-cooled French pressure cell (11.36×104 kg (30,0001b)IU$^{-2}$). EDTA was added to broken cells to a final concentration of 5 mM. Unbroken cells were removed by centrifugation at 17,000×g for 15 mins. The extract was further clarified by acidification to pH 5.0 at room temperature.

The protein concentration was first adjusted to 10 mg/ml and then the extract titrated to pH 5.0 with 2M acetic acid. The sample was left stirring for 15 mins and then the precipitate removed by centrifugation at 17,000×g for 15 mins. The supernatant was neutralised by addition of 1M Tris/HCl pH 8.0, dialysed into 25 mM Tris/HCl pH 8.0, 10 mM NaCl and applied to a DEAE-Sepharose (Trade Mark) column (2.6×8 cm). The column was eluted with a linear gradient of 10 mM–400 mM NaCl in 25 mM Tris/HCl pH 8.0. Fractions containing fragment C were pooled and dialysed into 25 mM Tris/HCl, 10 mM NaCl. The dialysed sample was titrated to pH 5.2 with 2M acetic acid just prior to application to an S-Sepharose column (1.6×7 cm) equilibrated with 25 mM acetate pH 5.2. A fine precipitate was generated which was removed by centrifugation with little loss of fragment C.

After sample application the column was eluted with a linear gradient of 10 mM–400 mM NaCl. Fragment C containing fractions were pooled and dialysed into 25 mM Tris/HCl pH 8.0, 10 mM NaCl. The final chromatography was on a Q-Sepharose column (1.6×7 cm), elution again being achieved with a linear 10 mM-400 mM NaCl gradient in 25 mM Tris/HCl pH 8.0. The peak fractions were pooled, concentrated and dialysed into 50 mM Tris/HCl pH 7.6, 0.2M NACl, 0.1 mM EDTA samples at a final protein concentration of 2–3 mg/ml were stored either at 4° C. or −70° C.

Protein Assays

A two antibody sandwich enzyme-linked immunosorbent assay (ELISA) for fragment C was developed. Purified pepsinised antibody prepared from horses hyperimmunised with tetanus toxoid (Hughes et al J. Appl. Bact. 3–7, 1974, 603–622) was used to coat flexible polyvinylchloride microtitre plates (Dynatech, Billingshurst, GB). Coating was performed overnight at 4° C. in 50 mM sodium carbonate pH 9.5 (12.5 μg pepsinised antibody per ml, 100 μl per well). Plates were washed three times with phosphate buffered saline pH 7.2, 0.12 (w/v) Tween (Trade Mark) 20 (PBS-Tween). Non-specific binding was reduced by incubation of plates with PBS-Tween containing 12 (wt/vol) BSA or 5% (wt/vol) non-fat dry milk. Plates were then incubated sequentially with antigen, second antibody and anti-rat IgG peroxidase conjugate (Kinkegaard and Perry, Maryland, US) for 1 hr at 37° C. in each case, The second antibody was a rat monoclonal (TT09) which binds with high affinity to fragment C (Sheppard et al, Infect. Immun. 43, 1984, 710–714) and it was used at a concentration of 2 μg/ml.

Anti-rat peroxidase conjugate was used at a dilution of 1:3000. Each reagent was diluted into PBS-Tween containing 5% non-fat dry milk prior to addition to plates. Plates were washed three times with PBS-Tween after each incubation. Bound enzyme complex was assayed using tetramethyl benzidine (TMB) as the chromogenic substrate. 1 mg TMB tablets (Wellcome Diagnostics) were dissolved in 10 ml of 0.0625M trisodium citrate containing 0.01% hydrogen peroxide. 100 reagent was added to each well and the reaction terminated μl of reagent was added to each well and the reaction terminated by addition of μl 2M $H_2SO_4$ after incubation for 10–15 mins at room temperature. Plates were read using a Titertek multiskan plate reader (MCC/340) at 450 nm.

For quantitation fragment C prepared from *C. tetani* (Fairweather et al, 1986) was used as a standard. Several dilutions of this fragment C gave a narrow range titration curve with linear portion between about 1 μg/ml and 10 μg/ml. Titration curves for the recombinant fragment C were comparable with similar slope and range to the standard curve. The titre of unknown samples was determined either by comparing the midpoints of titration curves or more routinely by reading directly from the linear portion of the standard curve. During purification, chromatographic fractions were screened for fragment C by immunodiffusion in 1% (wt/vol) agarose gels containing pepsinised horse antibody (approximately 0.25 mg/ml). Protein was determined using the BCA assay reagent (Pierce) with bovine serum albumin as protein standard.

2. RESULTS

Expression of fragment C in *E. coli*

Fragment C was expressed in *E. coli* using the two plasmids pTETtac1 and pTETtac2. pTETtac1 encodes tetanus toxin residues 537 to 864 (a portion of fragment B) and residues 865 to 1315 (fragment C). The numbering of the residues is according to Eisel et a, EMBO J. 5, 2495–2502, 1986 and Fairweather and Lyness, Nuc. Acid Res. 14, 7809–7812, 1986. *E. coli* cultures harbouring pTETtac1 were induced for expression of the tetanus fragments and were analysed by sodium dodecyl sulphate-polyacrylamide gel electrophoresis (SDS-PAGE). pTETtac1 expressed moderate levels of a 90 kD protein (FIG. 2) as predicted from the nucleotine sequence of tetanus toxin (Fairweather and Lyness, 1986). Confirmation of this 90 kD band as a tetanus toxin fragment was obtained by Western blotting against anti-fragment C sera (FIG. 2). After breakage of the cells and high speed centrifugation of the extract, most of the 90 kD protein was found to be in the pellet fraction (FIG. 2) as has been described for another fragment of tetanus toxin expressed in *E. coli* (Fairweather et al, 1986).

Plasmid pTETtac2 was predicted to express a 50 kD polypeptide which exactly corresponds to fragment C but with an additional methionine residue at the N-terminus. As shown in FIG. 2, induction of cells containing pTETtac2 resulted in expression of a protein of the correct size and which is recognised by anti-fragment C antisera (FIG. 2). The level of expression of pTETtac2 was higher than that of pTETtac1. Essentially all of the product was found in the soluble fraction after high speed centrifugation of cell extracts (FIG. 2). The levels of fragment C expressed by *E. coli* harbouring pTETtac2 and grown on a laboratory scale were determined by ELISA. Approximately 12 mg fragment C was obtained per liter of culture corresponding to approximately 3% total cell protein (Table 2).

Purification and characterisation of fragment C produced in *E. coli*

Fragment C produced in *E. coli* was purified using a combination of acid precipitation and ion exchange steps. No evidence of any heterogeneity was observed during chromatography. The results of the purification procedure are summarized in Table 2. There were still some minor *E. coli* contaminants after the final step and the overall purity was estimated to be 85% by densitometry of SDS-polyacrylamide gel electrophoresis (FIG. 3A, lane 2). The overall yield was about 50%.

Fragment C derived from *E. coli* and *C. tetani* were compared by electrophoretic analysis. Under non-reducing conditions on SDS-PAGE two bands of fragment C are seen in both preparations (FIG. 3A, lanes 4 and 5). The less intensely staining band co-migrates with reduced fragment C (FIG. 3A, lanes 2 and 3).

Preparations of recombinant fragment C showed a major Coomassie staining band on non-denaturing PAGE (FIG. 3B, lane 1) and isoelectric focussing gels (data not shown). The pI was determined to be 7.2. One or two additional minor species having more acidic pI's were occasionally seen. Heterogeneity was more apparent in preparations stored for prolonged periods (4 weeks or more) at 4° C. Fragment C from *C. tetani* shows three Coomassie staining bands of similar intensity on non-denaturing electrophoresis (FIG. 3B, lane 2) which co-migrate with the species seen in the recombinant preparation (lane 1). Such heterogeneity has previously been observed in fragment C from *C. tetani* (Helting and Zwisler, 1977) and was thought to be due to deamidation.

The immunogenicity of fragment C produced from *E. coli* and *C. tetani* was compared by immunising mice with vaccines containing fragment C followed by challenge with tetanus toxin. Table 1 shows that both preparations gave excellent protection against challenge, indicating similar protective potency of the two samples.

Immunisation of mice with fragment C

| Dilution of fragment C [(a)] | Number of Survivors [(b)] C. tetani | E. coli |
|---|---|---|
| 1/20 | 10/10 | 10/10 |
| 1/40 | 10/10 | 10/10 |
| 1/80 | 4/10 | 5/10 |
| 1/160 | 1/10 | 2/10 |
| 1/320 | 0/10 | 0/10 |

[(a)] Fragment C from *E. coli* (45 μg/ml) or from *C. tetani* (30 μg/ml) was diluted as indicated and 0.5 ml injected into mice.
[(b)] Mice were challenged after 4 weeks with approximately 50 $LD_{50}$s tetanus toxin, and survivors counted after 4 days.

TABLE 2

Purification of recombinant Fragment C

| Step | Total Protein (mg) | Fragment C (mg) | Recovery % |
|---|---|---|---|
| Total lysate | 1030.0 | 29.6 | 100 |
| Acid clarified extract | 622.0 | 25.5 | 86 |
| DEAE-Sepharose | 134.0 | 23.6 | 80 |
| S-Sepharose | 29.7 | 17.6 | 59 |
| Q-Sepharose | 15.5 | 15.7 | 53 |

COMPARATIVE EXAMPLE

Expression plasmid pTet18 expresses a polypeptide which comprises Met-Asn-Ser-Arg-Gly followed by 121 residues of B fragment and all 451 carboxy-terminal residues of C fragment, i.e. residues Ser-744 to Asp-1315 of tetanus toxin (Fairweather et al, 1987). The solubility of this polypeptide in the cytoplasm of *E. coli* was assessed.

*E. coli* DHI carrying plasmid pTet18 was grown overnight in L-broth containing ampicillin (100 μg/ml). The cells were diluted 1 in 5 into fresh medium containing 60 μg/ml IPTG (isopropyl-p-D-thiogalactopyranoside) and were grown for 4 hours. The cells from 2 liters of culture were harvested by centrifugation at 6,000 rpm for 20 mins with a Sorval GS3 rotor, and the cell pellets were stored at −20° C. overnight. The pellets were thawed and suspended in a total of 32 ml of 25 mM Tris hydrochloride (pH8.0)-1 mM EDTA-0.2% (wt/vol) Nonidet P-40-100 mM PMSF-1 mg of lysozyme per ml.

The cells were incubated on ice for 2 h. 0.32 ml of 1M $MgSO_4$ and 0.8 ml DNase (1 mg/ml) were added, and incubation was continued for a further 2 h. The material was centrifuged at 13,000 rpm for 10 mins with a Sorvall SS34 rotor, and the pellet was suspended in 160 ml of 50 mM Tris hydrochloride (pH8.0)-5 mM EDTA-5 mM ethylene glycol-bis(β-aminoethyl ether)-N,N,N',N',-tetraacetic acid (EGTA)-1% (wt/vol) Nonidet P40. The material was centrifuged as before, and the pellet was suspended in 160 ml of 50 mM Tris hydrochloride (pH8.0)-0.5M KSCN-5 mM EDTA-5 mM EGTA. After centrifugation as before, the pellet was suspended in 40 ml of 0.85% (wt/vol) saline and dialyzed overnight against saline. At each centrifugation step, the pellets and supernatants were assayed for tetanus protein by SDS-PAGE and Western blotting using rabbit anti-C fragment sera. The tetanus specific protein pTet18 was always found in the insoluble fraction.

What we claim is:

1. A process for producing fragment C of tetanus toxin in soluble form, which process comprises:
   (i) culturing an *Escherichia coli* host cell transformed with an expression vector comprising a coding sequence consisting of a Met start codon immediately followed by a sequence encoding fragment C, wherein said culturing is effected under conditions such that said coding sequence is expressed and fragment C thereby produced in soluble form; and
   (ii) recovering said soluble fragment C from the cytoplasm of said *Escherichia coli* host cell.

2. The process according to claim 1 wherein said soluble fragment C has the amino acid sequence set forth in SEQ I.D. NO. 8.

3. The process according to claim 1 or 2 wherein said *Escherichia coli* host cell is selected from strains HB101, DH1 and MM294.

4. An *Escherichia coli* expression vector comprising a coding sequence consisting of a Met start codon immediately followed by a sequence encoding fragment C of tetanus toxin, wherein said vector expresses fragment C in soluble form when present in the cytoplasm of an *Escherichia coli* host cell.

5. The vector according to claim 4 wherein said fragment C has the amino acid sequence set forth in SEQ ID No. 8.

6. An *Escherichia coli* host cell transformed with an expression vector as claimed in claim 4 or 5, wherein said fragment C is expressed in soluble form in the cytoplasm of said host cell.

7. The *Escherichia coli* host cell according to claim 6 wherein said host cell is selected from strains HB101, DH1 and MM294.

* * * * *

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
( A ) LENGTH: 44 base pairs
( B ) TYPE: nucleic acid
( C ) STRANDEDNESS: single
( D ) TOPOLOGY: linear ( i i ) MOLECULE TYPE: DNA ( v i ) ORIGINAL SOURCE:
( A ) ORGANISM: Clostridium tetani ( i x ) FEATURE:
( A ) NAME/KEY: CDS
( B ) LOCATION: 2..38

( x i ) SEQUENCE DESCRIPTION: SEQ ID NO:1:

```
C TTT GTT CCA ACC GAT GAA GGT TGG ACC AAC GAT TAA G GATCCG         44
  Phe Val Pro Thr Asp Glu Gly Trp Thr Asn Asp  *
  1               5                   10
```

( 2 ) INFORMATION FOR SEQ ID NO:2:

( i ) SEQUENCE CHARACTERISTICS:
( A ) LENGTH: 11 amino acids
( B ) TYPE: amino acid
( D ) TOPOLOGY: linear ( i i ) MOLECULE TYPE: protein ( x i ) SEQUENCE DESCRIPTION: SEQ ID NO:2:

```
Phe Val Pro Thr Asp Glu Gly Trp Thr Asn Asp
 1               5                   10
```

( 2 ) INFORMATION FOR SEQ ID NO:3:

( i ) SEQUENCE CHARACTERISTICS:
( A ) LENGTH: 44 base pairs
( B ) TYPE: nucleic acid
( C ) STRANDEDNESS: single
( D ) TOPOLOGY: linear ( i i ) MOLECULE TYPE: DNA ( v i ) ORIGINAL SOURCE:
( A ) ORGANISM: Clostridium tetani ( x i ) SEQUENCE DESCRIPTION: SEQ ID NO:3:

```
CTAGCGGATC CTTAATCGTT GGTCCAACCT TCATCGGTTG GAAC                   44
```

( 2 ) INFORMATION FOR SEQ ID NO:4:

( i ) SEQUENCE CHARACTERISTICS:
( A ) LENGTH: 161 base pairs
( B ) TYPE: nucleic acid
( C ) STRANDEDNESS: single
( D ) TOPOLOGY: linear ( i i ) MOLECULE TYPE: DNA ( v i ) ORIGINAL SOURCE:
( A ) ORGANISM: Clostridium tetani ( i x ) FEATURE:
( A ) NAME/KEY: CDS
( B ) LOCATION: 30..161

( x i ) SEQUENCE DESCRIPTION: SEQ ID NO:4:

| GAT CTT AAT C | ATC CAC AGG A | GAC TTT CTG | ATG | AAA | AAC | CTT | GAT | TGT | TGG | GTC | 53 |
| | | | Met | Lys | Asn | Leu | Asp | Cys | Trp | Val | |
| | | | 1 | | | | 5 | | | | |

| GAC | AAC | GAA | GAA | GAC | ATC | GAT | GTT | ATC | CTG | AAA | AAG | TCT | ACC | ATT | CTG | 101 |
| Asp | Asn | Glu | Glu | Asp | Ile | Asp | Val | Ile | Leu | Lys | Lys | Ser | Thr | Ile | Leu | |
| | 10 | | | | 15 | | | | 20 | | | | | | | |

| AAC | TTG | GAC | ATC | AAC | AAC | GAT | ATT | ATC | TCC | GAC | ATC | TCT | GGT | TTC | AAC | 149 |
| Asn | Leu | Asp | Ile | Asn | Asn | Asp | Ile | Ile | Ser | Asp | Ile | Ser | Gly | Phe | Asn | |
| 25 | | | | 30 | | | | | 35 | | | | | | 40 | |

| TCC | TCT | GTT | ATC | 161 |
| Ser | Ser | Val | Ile | |

( 2 ) INFORMATION FOR SEQ ID NO:5:

( i ) SEQUENCE CHARACTERISTICS:
        ( A ) LENGTH: 44 amino acids
        ( B ) TYPE: amino acid
        ( D ) TOPOLOGY: linear ( i i ) MOLECULE TYPE: protein ( x i ) SEQUENCE DESCRIPTION: SEQ ID NO:5:

| Met | Lys | Asn | Leu | Asp | Cys | Trp | Val | Asp | Asn | Glu | Glu | Asp | Ile | Asp | Val |
| 1 | | | | 5 | | | | | 10 | | | | | 15 | |

| Ile | Leu | Lys | Lys | Ser | Thr | Ile | Leu | Asn | Leu | Asp | Ile | Asn | Asn | Asp | Ile |
| | | | 20 | | | | | 25 | | | | | 30 | | |

| Ile | Ser | Asp | Ile | Ser | Gly | Phe | Asn | Ser | Ser | Val | Ile |
| | | 35 | | | | | 40 | | | | |

( 2 ) INFORMATION FOR SEQ ID NO:6:

( i ) SEQUENCE CHARACTERISTICS:
        ( A ) LENGTH: 161 base pairs
        ( B ) TYPE: nucleic acid
        ( C ) STRANDEDNESS: single
        ( D ) TOPOLOGY: linear ( i i ) MOLECULE TYPE: DNA ( v i ) ORIGINAL SOURCE:
        ( A ) ORGANISM: Clostridium tetani ( x i ) SEQUENCE DESCRIPTION: SEQ ID NO:6:

| ATGTGATAAC | AGAGGAGTTG | AAACCAGAGA | TGTCGGAGAT | AATATCGTTG | TTGATGTCCA | 60 |
| AGTTCAGAAT | GGTAGACTTT | TTCAGGATAA | CATCGATGTC | TTCTTCGTTG | TCGACCCAAC | 120 |
| AATCAAGGTT | TTTCATCAGA | AAGTCTCCTG | TGGATGATTA | A | | 161 |

( 2 ) INFORMATION FOR SEQ ID NO:7:

( i ) SEQUENCE CHARACTERISTICS:
        ( A ) LENGTH: 1359 base pairs
        ( B ) TYPE: nucleic acid
        ( C ) STRANDEDNESS: double
        ( D ) TOPOLOGY: linear ( i i ) MOLECULE TYPE: DNA ( v i ) ORIGINAL SOURCE:
        ( A ) ORGANISM: Clostridium tetani ( i x ) FEATURE:
        ( A ) NAME/KEY: CDS
        ( B ) LOCATION: 1..1359

( x i ) SEQUENCE DESCRIPTION: SEQ ID NO:7:

| ATG | AAA | AAC | CTT | GAT | TGT | TGG | GTC | GAC | AAC | GAA | GAA | GAC | ATC | GAT | GTT | 48 |

-continued

| | | | | | | | | | | | | | | | | |
|---|---|---|---|---|---|---|---|---|---|---|---|---|---|---|---|---|
| Met<br>1 | Lys | Asn | Leu | Asp<br>5 | Cys | Trp | Val | Asp | Asn<br>10 | Glu | Glu | Asp | Ile | Asp<br>15 | Val | |
| ATC<br>Ile | CTG<br>Leu | AAA<br>Lys | AAG<br>Lys<br>20 | TCT<br>Ser | AAC<br>Asn | ATT<br>Ile | CTG<br>Leu | AAC<br>Asn<br>25 | TTG<br>Leu | GAC<br>Asp | ATC<br>Ile | AAC<br>Asn | AAC<br>Asn<br>30 | GAT<br>Asp | ATT<br>Ile | 96 |
| ATC<br>Ile | TCC<br>Ser | GAC<br>Asp<br>35 | ATC<br>Ile | TCT<br>Ser | GGT<br>Gly | TCC<br>Ser | AAC<br>Asn<br>40 | TCC<br>Ser | TCT<br>Ser | AGG<br>Arg | ATC<br>Ile | ACA<br>Thr<br>45 | TAT<br>Tyr | CCA<br>Pro | GAT<br>Asp | 144 |
| GCT<br>Ala | CAA<br>Gln<br>50 | TTG<br>Leu | GTG<br>Val | CCC<br>Pro | GGA<br>Gly | ATA<br>Ile<br>55 | AAT<br>Asn | GGC<br>Gly | AAA<br>Lys | GCA<br>Ala | ATA<br>Ile<br>60 | CAT<br>His | TTA<br>Leu | GTA<br>Val | AAC<br>Asn | 192 |
| AAT<br>Asn<br>65 | GAA<br>Glu | TCT<br>Ser | TCT<br>Ser | GAA<br>Glu | GTT<br>Val<br>70 | ATA<br>Ile | GTG<br>Val | CAT<br>His | AAA<br>Lys | GCT<br>Ala<br>75 | ATG<br>Met | GAT<br>Asp | ATT<br>Ile | GAA<br>Glu | TAT<br>Tyr<br>80 | 240 |
| AAT<br>Asn | GAT<br>Asp | ATG<br>Met | TTT<br>Phe | AAT<br>Asn<br>85 | AAT<br>Asn | TTT<br>Phe | ACC<br>Thr | GTT<br>Val | AGC<br>Ser<br>90 | TTT<br>Phe | TGG<br>Trp | TTG<br>Leu | AGG<br>Arg | GTT<br>Val<br>95 | CCT<br>Pro | 288 |
| AAA<br>Lys | GTA<br>Val | TCT<br>Ser | GCT<br>Ala | AGT<br>Ser<br>100 | CAT<br>His | TTA<br>Leu | GAA<br>Glu | CAA<br>Gln | TAT<br>Tyr<br>105 | GGC<br>Gly | ACA<br>Thr | AAT<br>Asn | GAG<br>Glu | TAT<br>Tyr<br>110 | TCA<br>Ser | 336 |
| ATA<br>Ile | AAT<br>Asn | AGC<br>Ser<br>115 | TCT<br>Ser | ATG<br>Met | AAA<br>Lys | AAA<br>Lys | CAT<br>His<br>120 | AGT<br>Ser | CTA<br>Leu | TCA<br>Ser | ATA<br>Ile | GGA<br>Gly<br>125 | TCT<br>Ser | GGT<br>Gly | TGG<br>Trp | 384 |
| AGT<br>Ser | GTA<br>Val<br>130 | TCA<br>Ser | CTT<br>Leu | AAA<br>Lys | GGT<br>Gly | AAT<br>Asn<br>135 | AAC<br>Asn | TTA<br>Leu | ATA<br>Ile | TGG<br>Trp | ACT<br>Thr<br>140 | TTA<br>Leu | AAA<br>Lys | GAT<br>Asp | TCC<br>Ser | 432 |
| GCG<br>Ala<br>145 | GGA<br>Gly | GAA<br>Glu | GTT<br>Val | AGA<br>Arg | CAA<br>Gln<br>150 | ATA<br>Ile | ACT<br>Thr | TTT<br>Phe | AGG<br>Arg | GAT<br>Asp<br>155 | TTA<br>Leu | CCT<br>Pro | GAT<br>Asp | AAA<br>Lys | TTT<br>Phe<br>160 | 480 |
| AAT<br>Asn | GCT<br>Ala | TAT<br>Tyr | TTA<br>Leu | GCA<br>Ala<br>165 | AAT<br>Asn | AAA<br>Lys | TGG<br>Trp | GTT<br>Val | TTT<br>Phe<br>170 | ATA<br>Ile | ACT<br>Thr | ATT<br>Ile | ACT<br>Thr | AAT<br>Asn<br>175 | GAT<br>Asp | 528 |
| AGA<br>Arg | TTA<br>Leu | TCT<br>Ser<br>180 | TCT<br>Ser | GCT<br>Ala | AAT<br>Asn | TTG<br>Leu | TAT<br>Tyr<br>185 | ATA<br>Ile | AAT<br>Asn | GGA<br>Gly | GTA<br>Val | CTT<br>Leu<br>190 | ATG<br>Met | GGA<br>Gly | AGT<br>Ser | 576 |
| GCA<br>Ala | GAA<br>Glu<br>195 | ATT<br>Ile | ACT<br>Thr | GGT<br>Gly | TTA<br>Leu | GGA<br>Gly<br>200 | GCT<br>Ala | ATT<br>Ile | AGA<br>Arg | GAG<br>Glu | GAT<br>Asp<br>205 | AAT<br>Asn | AAT<br>Asn | ATA<br>Ile | ACA<br>Thr | 624 |
| TTA<br>Leu<br>210 | AAA<br>Lys | CTA<br>Leu | GAT<br>Asp | AGA<br>Arg | TGT<br>Cys<br>215 | AAT<br>Asn | AAT<br>Asn | AAT<br>Asn | AAT<br>Asn | CAA<br>Gln<br>220 | TAC<br>Tyr | GTT<br>Val | TCT<br>Ser | ATT<br>Ile | GAT<br>Asp | 672 |
| AAA<br>Lys<br>225 | TTT<br>Phe | AGG<br>Arg | ATA<br>Ile | TTT<br>Phe | TGC<br>Cys<br>230 | AAA<br>Lys | GCA<br>Ala | TTA<br>Leu | AAT<br>Asn | CCA<br>Pro<br>235 | AAA<br>Lys | GAG<br>Glu | ATT<br>Ile | GAA<br>Glu | AAA<br>Lys<br>240 | 720 |
| TTA<br>Leu | TAC<br>Tyr | ACA<br>Thr | AGT<br>Ser | TAT<br>Tyr<br>245 | TTA<br>Leu | TCT<br>Ser | ATA<br>Ile | ACC<br>Thr | TTT<br>Phe<br>250 | TTA<br>Leu | AGA<br>Arg | GAC<br>Asp | TTC<br>Phe | TGG<br>Trp<br>255 | GGA<br>Gly | 768 |
| AAC<br>Asn | CCT<br>Pro | TTA<br>Leu | CGA<br>Arg<br>260 | TAT<br>Tyr | GAT<br>Asp | ACA<br>Thr | GAA<br>Glu | TAT<br>Tyr<br>265 | TAT<br>Tyr | TTA<br>Leu | ATA<br>Ile | CCA<br>Pro | GTA<br>Val<br>270 | GCT<br>Ala | TCT<br>Ser | 816 |
| AGT<br>Ser | TCT<br>Ser | AAA<br>Lys<br>275 | GAT<br>Asp | GTT<br>Val | CAA<br>Gln | TTG<br>Leu | AAA<br>Lys<br>280 | AAT<br>Asn | ATA<br>Ile | ACA<br>Thr | GAT<br>Asp | TAT<br>Tyr<br>285 | ATG<br>Met | TAT<br>Tyr | TTG<br>Leu | 864 |
| ACA<br>Thr | AAT<br>Asn<br>290 | GCG<br>Ala | CCA<br>Pro | TCG<br>Ser | TAT<br>Tyr | ACT<br>Thr<br>295 | AAC<br>Asn | GGA<br>Gly | AAA<br>Lys | TTG<br>Leu | AAT<br>Asn<br>300 | ATA<br>Ile | TAT<br>Tyr | TAT<br>Tyr | AGA<br>Arg | 912 |
| AGG<br>Arg<br>305 | TTA<br>Leu | TAT<br>Tyr | AAT<br>Asn | GGA<br>Gly | CTA<br>Leu<br>310 | AAA<br>Lys | TTT<br>Phe | ATT<br>Ile | ATA<br>Ile | AAA<br>Lys<br>315 | AGA<br>Arg | TAT<br>Tyr | ACA<br>Thr | CCT<br>Pro | AAT<br>Asn<br>320 | 960 |
| AAT<br>Asn | GAA<br>Glu | ATA<br>Ile | GAT<br>Asp | TCT<br>Ser<br>325 | TTT<br>Phe | GTT<br>Val | AAA<br>Lys | TCA<br>Ser | GGT<br>Gly<br>330 | GAT<br>Asp | TTT<br>Phe | ATT<br>Ile | AAA<br>Lys | TTA<br>Leu<br>335 | TAT<br>Tyr | 1008 |

```
GTA  TCA  TAT  AAC  AAT  AAT  GAG  CAC  ATT  GTA  GGT  TAT  CCG  AAA  GAT  GGA      1056
Val  Ser  Tyr  Asn  Asn  Asn  Glu  His  Ile  Val  Gly  Tyr  Pro  Lys  Asp  Gly
               340                      345                      350

AAT  GCC  TTT  AAT  AAT  CTT  GAT  AGA  ATT  CTA  AGA  GTA  GGT  TAT  AAT  GCC      1104
Asn  Ala  Phe  Asn  Asn  Leu  Asp  Arg  Ile  Leu  Arg  Val  Gly  Tyr  Asn  Ala
          355                      360                      365

CCA  GGT  ATC  CCT  CTT  TAT  AAA  AAA  ATG  GAA  GCA  GTA  AAA  TTG  CGT  GAT      1152
Pro  Gly  Ile  Pro  Leu  Tyr  Lys  Lys  Met  Glu  Ala  Val  Lys  Leu  Arg  Asp
     370                      375                      380

TTA  AAA  ACC  TAT  TCT  GTA  CAA  CTT  AAA  TTA  TAT  GAT  GAT  AAA  AAT  GCA      1200
Leu  Lys  Thr  Tyr  Ser  Val  Gln  Leu  Lys  Leu  Tyr  Asp  Asp  Lys  Asn  Ala
385                      390                      395                      400

TCT  TTA  GGA  CTA  GTA  GGT  ACC  CAT  AAT  GGT  CAA  ATA  GGC  AAC  GAT  CCA      1248
Ser  Leu  Gly  Leu  Val  Gly  Thr  His  Asn  Gly  Gln  Ile  Gly  Asn  Asp  Pro
                    405                      410                      415

AAT  AGG  GAT  ATA  TTA  ATT  GCA  AGC  AAC  TGG  TAC  TTT  AAT  CAT  TTA  AAA      1296
Asn  Arg  Asp  Ile  Leu  Ile  Ala  Ser  Asn  Trp  Tyr  Phe  Asn  His  Leu  Lys
               420                      425                      430

GAT  AAA  ATT  TTA  GGA  TGT  GAT  TGG  TAC  TTT  GTT  CCA  ACC  GAT  GAA  GGT      1344
Asp  Lys  Ile  Leu  Gly  Cys  Asp  Trp  Tyr  Phe  Val  Pro  Thr  Asp  Glu  Gly
          435                      440                      445

TGG  ACC  AAC  GAT  TAA                                                              1359
Trp  Thr  Asn  Asp
450
```

( 2 ) INFORMATION FOR SEQ ID NO:8:

( i ) SEQUENCE CHARACTERISTICS:
        ( A ) LENGTH: 452 amino acids
        ( B ) TYPE: amino acid
        ( D ) TOPOLOGY: linear ( i i ) MOLECULE TYPE: protein ( x i ) SEQUENCE DESCRIPTION: SEQ ID NO:8:

```
Met  Lys  Asn  Leu  Asp  Cys  Trp  Val  Asp  Asn  Glu  Glu  Asp  Ile  Asp  Val
  1                 5                     10                     15

Ile  Leu  Lys  Lys  Ser  Asn  Ile  Leu  Asn  Leu  Asp  Ile  Asn  Asn  Asp  Asn
               20                     25                     30

Ile  Ser  Asp  Ile  Ser  Gly  Ser  Asn  Ser  Ser  Arg  Ile  Thr  Tyr  Pro  Asp
          35                     40                     45

Ala  Gln  Leu  Val  Pro  Gly  Ile  Asn  Gly  Lys  Ala  Ile  His  Leu  Val  Asn
     50                     55                     60

Asn  Glu  Ser  Ser  Glu  Val  Ile  Val  His  Lys  Ala  Met  Asp  Ile  Glu  Tyr
 65                     70                     75                     80

Asn  Asp  Met  Phe  Asn  Asn  Phe  Thr  Val  Ser  Phe  Trp  Leu  Arg  Val  Pro
                85                     90                     95

Lys  Val  Ser  Ala  Ser  His  Leu  Glu  Gln  Tyr  Gly  Thr  Asn  Glu  Tyr  Ser
               100                    105                    110

Ile  Asn  Ser  Ser  Met  Lys  Lys  His  Ser  Leu  Ser  Ile  Gly  Ser  Gly  Trp
          115                    120                    125

Ser  Val  Ser  Leu  Lys  Gly  Asn  Asn  Leu  Ile  Trp  Thr  Leu  Lys  Asp  Ser
     130                    135                    140

Ala  Gly  Glu  Val  Arg  Gln  Ile  Thr  Phe  Arg  Asp  Leu  Pro  Asp  Lys  Phe
145                    150                    155                    160

Asn  Ala  Tyr  Leu  Ala  Asn  Lys  Trp  Val  Phe  Ile  Thr  Ile  Thr  Asn  Asp
               165                    170                    175

Arg  Leu  Ser  Ser  Ala  Asn  Leu  Tyr  Ile  Asn  Gly  Val  Leu  Met  Gly  Ser
          180                    185                    190

Ala  Glu  Ile  Thr  Gly  Leu  Gly  Ala  Asn  Arg  Glu  Asp  Asn  Asn  Ile  Thr
```

|     |     |     | 195 |     |     |     | 200 |     |     |     |     | 205 |     |     |
| --- | --- | --- | --- | --- | --- | --- | --- | --- | --- | --- | --- | --- | --- | --- |
| Leu | Lys 210 | Leu | Asp | Arg | Cys | Asn 215 | Asn | Asn | Asn | Gln | Tyr 220 | Val | Ser | Asn | Asp |
| Lys 225 | Phe | Arg | Ile | Phe | Cys 230 | Lys | Ala | Leu | Asn | Pro 235 | Lys | Glu | Ile | Glu | Lys 240 |
| Leu | Tyr | Thr | Ser | Tyr 245 | Leu | Ser | Ile | Thr | Phe 250 | Leu | Arg | Asp | Phe | Trp 255 | Gly |
| Asn | Pro | Leu | Arg 260 | Tyr | Asp | Thr | Glu | Tyr 265 | Tyr | Leu | Ile | Pro | Val 270 | Ala | Ser |
| Ser | Ser | Lys 275 | Asp | Val | Gln | Leu | Lys 280 | Asn | Ile | Thr | Asp | Tyr 285 | Met | Tyr | Leu |
| Thr | Asn 290 | Ala | Pro | Ser | Tyr | Thr 295 | Asn | Gly | Lys | Leu | Asn 300 | Ile | Tyr | Tyr | Arg |
| Arg 305 | Leu | Tyr | Asn | Gly | Leu 310 | Lys | Phe | Ile | Ile | Lys 315 | Arg | Tyr | Thr | Pro | Asn 320 |
| Asn | Glu | Ile | Asp | Ser 325 | Phe | Val | Lys | Ser | Gly 330 | Asp | Phe | Ile | Lys | Leu 335 | Tyr |
| Val | Ser | Tyr | Asn 340 | Asn | Asn | Glu | His | Ile 345 | Val | Gly | Tyr | Pro | Lys 350 | Asp | Gly |
| Asn | Ala | Phe 355 | Asn | Asn | Leu | Asp | Arg 360 | Ile | Leu | Arg | Val | Gly 365 | Tyr | Asn | Ala |
| Pro | Gly 370 | Ile | Pro | Leu | Tyr | Lys 375 | Lys | Met | Glu | Ala | Val 380 | Lys | Leu | Arg | Asp |
| Leu 385 | Lys | Thr | Tyr | Ser | Val 390 | Gln | Leu | Lys | Leu | Tyr 395 | Asp | Asp | Lys | Asn | Ala 400 |
| Ser | Leu | Gly | Leu | Val 405 | Gly | Thr | His | Asn | Gly 410 | Gln | Ile | Gly | Asn | Asp 415 | Pro |
| Asn | Arg | Asp | Ile 420 | Leu | Ile | Ala | Ser | Asn 425 | Trp | Tyr | Phe | Asn | His 430 | Leu | Lys |
| Asp | Lys | Ile 435 | Leu | Gly | Cys | Asp | Trp 440 | Tyr | Phe | Val | Pro | Thr 445 | Asp | Glu | Gly |
| Trp | Thr 450 | Asn | Asp |     |     |     |     |     |     |     |     |     |     |     |     |